(12) United States Patent
Tong et al.

(10) Patent No.: US 10,814,145 B2
(45) Date of Patent: Oct. 27, 2020

(54) SYSTEMS AND METHODS FOR CORRECTING A POSITION ERROR OF A MOTION TERMINAL

(71) Applicant: SHANGHAI UNITED IMAGING HEALTHCARE CO., LTD., Shanghai (CN)

(72) Inventors: Liuzhu Tong, Shanghai (CN); Boqi Ma, Shanghai (CN); Yujie Chen, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 168 days.

(21) Appl. No.: 15/939,320

(22) Filed: Mar. 29, 2018

(65) Prior Publication Data

US 2019/0151681 A1 May 23, 2019

(30) Foreign Application Priority Data

Nov. 21, 2017 (CN) .......................... 2017 1 1168186

(51) Int. Cl.
*A61N 5/10* (2006.01)

(52) U.S. Cl.
CPC ......... *A61N 5/1045* (2013.01); *A61N 5/1075* (2013.01); *A61N 5/1081* (2013.01); *A61N 5/1065* (2013.01)

(58) Field of Classification Search
CPC .. A61N 5/1045; A61N 5/1049; A61N 5/1048; A61N 5/1036; A61N 5/1064; A61N 5/1084
See application file for complete search history.

(56) References Cited

U.S. PATENT DOCUMENTS

| | | | | |
|---|---|---|---|---|
| 4,885,998 A | * | 12/1989 | Span | A61B 6/0457 |
| | | | | 108/139 |
| 2005/0185766 A1 | | 8/2005 | Tsujita | |
| 2013/0025391 A1 | | 1/2013 | Magnusson | |
| 2014/0184888 A1 | | 7/2014 | Won et al. | |
| 2016/0361567 A1 | * | 12/2016 | Chappelow | A61N 5/1048 |
| 2018/0035969 A1 | * | 2/2018 | Jin | A61N 5/10 |

FOREIGN PATENT DOCUMENTS

| | | |
|---|---|---|
| CN | 102997841 A | 3/2013 |
| CN | 103185947 A | 7/2013 |
| CN | 103301582 A | 9/2013 |
| JP | 2000159134 A | 6/2000 |
| JP | 2002253686 A | 9/2002 |

* cited by examiner

*Primary Examiner* — David P Porta
*Assistant Examiner* — Fani Boosalis
(74) *Attorney, Agent, or Firm* — Metis IP LLC

(57) ABSTRACT

A method for correcting a position error for a motion terminal driven by a driving component may include obtaining a first displacement of the motion terminal acquired by a first sensor associated with the driving component. The method may also include obtaining a second displacement of the motion terminal acquired by a second sensor associated with the motion terminal. The method may further include determining an offset value based on a difference between the first displacement and the second displacement. The method may include determining a calibration displacement value relating to the first displacement based on the offset value.

20 Claims, 11 Drawing Sheets

1100

SYSTEMS AND METHODS FOR CORRECTING A POSITION ERROR OF A MOTION TERMINAL

CROSS-REFERENCE TO RELATED APPLICATIONS

This application claims priority to Chinese Patent Application No. 201711168186.1 filed on Nov. 21, 2017, the entire contents of which are hereby incorporated by reference.

TECHNICAL FIELD

The present disclosure generally relates to a medical treatment system and more specifically, relates to systems and methods for correcting position errors of a motion terminal in a radiotherapy procedure.

BACKGROUND

In a radiotherapy device, when a driving component drives a motion terminal to a target position by a transmission device (e.g., a screw drive or a gear drive), a position error caused by a backlash may be generated. Due to a manufacturing error, it is a common question when a motion terminal is driven by the transmission drive. For example, the screw drive may include a screw rod and a screw nut. When the screw rod changes its direction, the screw nut may not move until the backlash is eliminated. That is to say, the movement of the screw nut may lag behind the movement of the screw rod. A backlash error may be generated. Therefore, the backlash error may decrease the positioning accuracy of the motion terminal. For a radiotherapy treatment, it is necessary to control motion accuracy to achieve precise positioning of each component (e.g., a primary collimator, a jaw, or each leaf of a multi-leaf collimator) in a treatment head. For example, each leaf of a multi-leaf collimator (MLC) of a radiotherapy device may need to be driven to a target position accurately for scaling a radiation field. Therefore, it is desirable to provide a system and method for correcting a position error of a motion terminal to achieve higher motion accuracy.

SUMMARY

According to another aspect of the present disclosure, a method for correcting a position error for a motion terminal driven by a driving component is provided. The method may include obtaining a first displacement of the motion terminal acquired by a first sensor associated with the driving component and obtaining a second displacement of the motion terminal acquired by a second sensor associated with the motion terminal. The method may also include determining an offset value based on a difference between the first displacement and the second displacement. The method may further determining a calibration displacement value relating to the first displacement based on the offset value.

In some embodiments, the determining an offset value based on a difference between the first displacement and the second displacement may include determining the difference between the first displacement and the second displacement, comparing the difference between the first displacement and the second displacement with an upper threshold relating to the position error of the motion terminal, and determining a smaller value of an absolute value of both the difference and the upper threshold as the offset value.

In some embodiments, the method may further include determining a plurality of measured values relating to the position error of the motion terminal, determining an average value of the plurality of measured values relating to the position error of the motion terminal, and determining the upper threshold based on the plurality of measured values relating to a position error of the motion terminal, the upper threshold being greater than the average value and less than a maximum value of the plurality of measured values relating to the position error of the motion terminal.

In some embodiments, the method may further include determining a plurality of measured values relating to the position error of the motion terminal, determining an average value of the plurality of measured values relating to the position error of the motion terminal, and determining a product of the average value and a safety factor as the threshold.

In some embodiments, the method may further include determining a target position of the motion terminal based on the calibration displacement value.

In some embodiments, the first sensor may include an encoder.

In some embodiments, the second sensor may include a Hall sensor.

According to an aspect of the present disclosure, a system for correcting a position error for a motion terminal driven by a driving component is provided. The system may include a motion terminal, a transmission component, a driving component configured to drive the motion terminal to move based on the transmission component, a first sensor associated with the driving component, the first sensor being configured to acquire a first movement displacement of the motion terminal inputted by the driving component, and a second sensor associated with the motion terminal, the second sensor being configured to acquire a second movement displacement of the motion terminal. The system may also include a storage device storing a set of instructions and one or more processors in communication with the storage device. When executing the instructions, one or more processors may be configured to cause the system to obtain the first displacement of the motion terminal acquired by the first sensor associated with the driving component and obtain the second displacement of the motion terminal acquired by the second sensor associated with the motion terminal. The one or more processors may also determine an offset value based on a difference between the first displacement and the second displacement. The one or more processors may further determine a calibration displacement value relating to the first displacement based on the offset value.

According to an aspect of the present disclosure, a system for correcting a position error is provided. The system may include a radiation source, a multi-leaf collimator including a plurality of leaves configured to collimate a radiation field, a driving component configured to drive a leaf to move, a first sensor associated with the driving component, the first sensor being configured to acquire a first movement displacement of the leaf inputted by the driving component, and a second sensor associated with the leaf to move, the second sensor being configured to acquire a second movement displacement of the each of the plurality of leaves. The system may also include a storage device storing a set of instructions and one or more processors in communication with the storage device. When executing the instructions, one or more processors may be configured to cause the system to obtain the first displacement of the leaf acquired by the first sensor associated with the driving component and obtain the second displacement of the leaf acquired by the second sensor associated with the each of the plurality of leaves. The one or more processors may also determine an offset value based on a difference between the first displacement and the second displacement. The one or more processors may further determine a calibration displacement value relating to the first displacement based on the offset value.

According to another aspect of the present disclosure, a non-transitory computer readable medium may include instructions. When executed by at least one processor, the executions may cause the at least one processor to implement a method for detecting abnormal scene. The method may include obtaining a first displacement of the motion terminal acquired by a first sensor associated with the driving component and obtaining a second displacement of the motion terminal acquired by a second sensor associated with the motion terminal. The method may also include determining an offset value based on a difference between the first displacement and the second displacement. The method may further determining a calibration displacement value relating to the first displacement based on the offset value.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
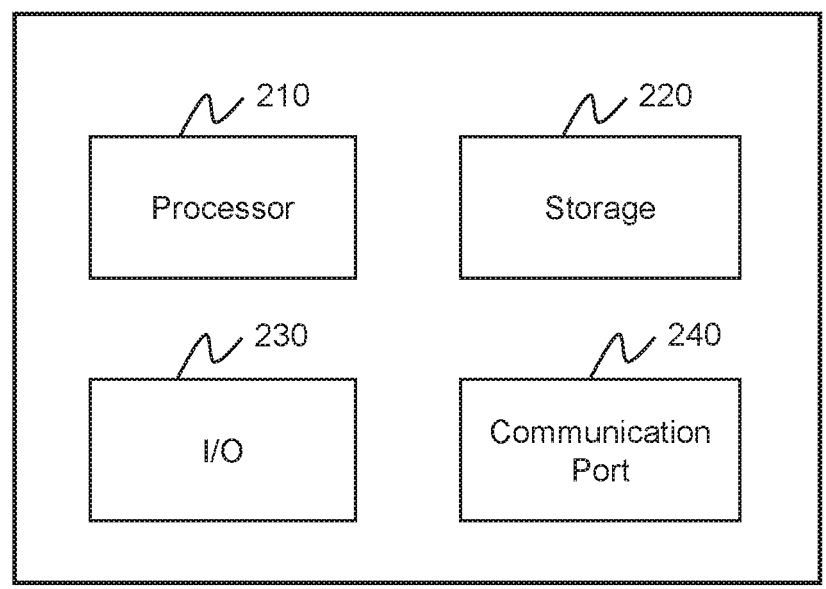
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

The present disclosure may provide a system and a method for correcting a position error of motion terminal. More particularly, a processor may obtain a first displacement of the motion terminal. The first displacement may be acquired by a first sensor associated with a driving component. The processor may obtain a second displacement of the motion terminal. The second displacement may be acquired by a second sensor associated with the motion terminal. The first displacement may include an instruction displacement output by the driving component. The second displacement may include an actual displacement of the motion terminal, when the driving component drives the motion terminal to a target position. To correct a position error of the motion terminal, the processor may determine an offset value based on a difference between the first displacement and the second displacement. The processor may further determine a calibration displacement value relating to the first displacement based on the offset value. Then the driving component may drive the motion terminal to a target position based on the calibration displacement value.

Figure 1:
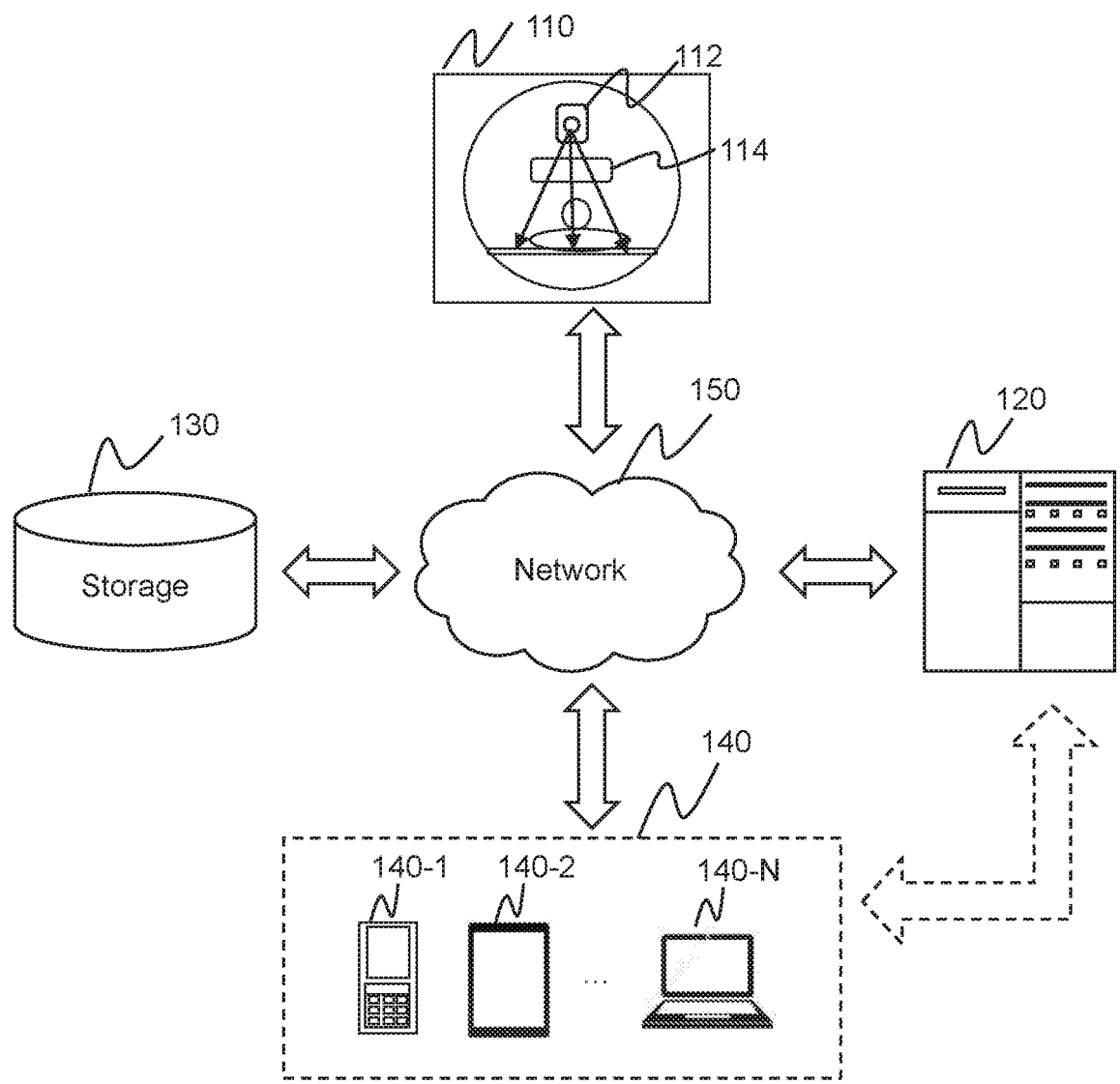
FIG. 1 is a schematic diagram illustrating an exemplary radiotherapy system according to some embodiments of the present disclosure.

FIG. 1 is a schematic diagram illustrating an exemplary radiotherapy system 100 according to some embodiments of the present disclosure. As shown, the radiotherapy system 100 may include a radiotherapy device 110, a processing device 120, a storage 130, one or more terminal(s) 140 and a network 150. In some embodiments, the radiotherapy device 110, the processing device 120, the storage 130, and/or the terminal(s) 140 may be connected to and/or communicate with each other via a wireless connection (e.g., the network 150), a wired connection, or a combination thereof. The connections between the components in the radiotherapy system 100 may be variable. Merely by way of example, the radiotherapy device 110 may be connected to the processing device 120 through the network 150, as illustrated in FIG. 1. As another example, the radiotherapy device 110 may be connected to the processing device 120 directly. As a further example, the storage 130 may be connected to the processing device 120 through the network 150, as illustrated in FIG. 1, or connected to the processing device 120 directly. As still a further example, the terminals) 140 may be connected to the processing device 120 through the network 150, as illustrated in FIG. 1, or connected to the processing device 120 directly (as indicated by the bidirectional arrow in dashed line shown in FIG. 1), or connected to the radiotherapy device 110 directly or through the network 150. The terminals) 140 may be omitted.

The radiotherapy device 110 may perform radiotherapy treatment on at least one part of a subject. The radiotherapy device 110 may include a treatment plan system (TPS), an image-guide radio therapy (IGRT) system, etc. Merely by way of example, the image-guided radio therapy (IGRT) system may include, for example, a CT guided radiotherapy system, an MRI guided radiotherapy system, etc. In some embodiments, the radiotherapy device 110 may include a single modality apparatus, for example, an X-ray therapy apparatus, a Co-60 teletherapy apparatus, a medical electron accelerator, etc. In some embodiments, the radiotherapy device 110 may be a multi-modality (e.g., two-modality) apparatus to acquire a medical image relating to the at least one part of the subject and perform radiotherapy treatment on the at least one part of the subject. The subject may be biological or non-biological. For example, the subject may include a patient, a man-made object, etc. As another example, the subject may include a specific portion, organ, and/or tissue of the patient. For example, the subject may include head, neck, thorax, cardiac, stomach, blood vessel, soft tissue, tumor, nodules, or the like, or a combination thereof. In some embodiments, the subject may include a region of interest (ROI), such as a tumor, a node, etc.

In some embodiments, the radiotherapy device 110 may include a gantry to which a treatment head may be connected. The treatment head may include a radiation source 112 and a multi-leaf collimator (MLC) 114. The radiation source 112 may emit radiation beams to a subject. The MLC 114 may be configured to collimate radiation beams emitted from the radiation source 112. In some embodiments, the MLC 114 may include a plurality of leaves to scale a radiation field. The plurality of leaves may be driven by one or more driving components (e.g., motors) to move to target positions to expand or narrow the radiation field. More particularly, the driving component may actuate one or more transmission device(s) connected to the MLC so as to further drive the leaves of the MLC. In some embodiments, the transmission device may include a gear drive, a screw drive, a belt drive, or the like, or any combination thereof. However, due to the mechanical factors associated with the one or more driving components (e.g., the motors), an actual position of a leaf may be inconsistent with an target position specified by the processing device 120, which causes a position error between the actual position and the target position. The position error of a leaf may be caused by a backlash error relating to a driving component, leaf deformation, leaf positioning, horizontality, perpendicularity, or the like, or any combination thereof. More detail descriptions about the MLC are disclosed elsewhere in this application (e.g., FIG. 7 and the descriptions thereof).

The processing device 120 may process data and/or information obtained from the radiotherapy device 110, the storage 130, and/or the terminal(s) 140. For example, the processing device 120 may execute instructions to drive the driving component (e.g., the motor) control a movement displacement of each of the plurality of leaves in the MLC 114. As another example, the processing device 120 may determine an offset value of each of a plurality of leaves in the MLC 114, and determine a calibration displacement value according to the determined offset value. As a further example, the processing device 120 may determine a target position of the each of the plurality of leaves in the MLC 114 based on the calibration displacement value.

In some embodiments, the processing device 120 may be a single server or a server group. The server group may be centralized or distributed. In some embodiments, the processing device 120 may be local or remote. For example, the processing device 120 may access information and/or data from the radiotherapy device 110, the storage 130, and/or the terminal(s) 140 via the network 150. As another example, the processing device 120 may be directly connected to the radiotherapy device 110, the terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an intercloud, a multi-cloud, or the like, or a combination thereof. In some embodiments, the processing device 120 may be implemented by a mobile device 400 having one or more components as described in connection with FIG. 4.

The storage 130 may store data, instructions, and/or any other information. In some embodiments, the storage 130 may store data obtained from the radiotherapy device 110, the processing device 120, and/or the terminal(s) 140. In some embodiments, the storage 130 may store data and/or instructions that the processing device 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the radiotherapy system 100 (e.g., the processing device 120, the terminal(s) 140, etc.). One or more components in the radiotherapy system 100 may access the data or instructions stored in the storage 130 via the network 150. In some embodiments, the storage 130 may be part of the processing device 120.

The terminal(s) 140 may be connected to and/or communicate with the radiotherapy device 110, the processing device 120, and/or the storage 130. For example, the terminal(s) 140 may obtain a processed image from the processing device 120. As another example, the terminal(s) 140 may obtain image data acquired via the radiotherapy device 110 and transmit the image data to the processing device 120 to be processed. In some embodiments, the terminal(s) 140 may include a mobile device 140-1, a tablet computer 140-2, . . . , a laptop computer 140-N, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the radiotherapy system 100. In some embodiments, one or more components of the radiotherapy system 100 (e.g., the radiotherapy device 110, the processing device 120, the storage 130, the terminal(s) 140, etc.) may communicate information and/or data with one or more other components of the radiotherapy system 100 via the network 150. For example, the processing device 120 may obtain image data from the radiotherapy device 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the radiotherapy system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. As another example, the radiotherapy system 100 may further include a treatment planning system. However, those variations and modifications do not depart the scope of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process data obtained from the radiotherapy device 110, the storage 130, terminal(s) 140, and/or any other component of the radiotherapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the radiotherapy device 110, the storage 130, the terminal(s) 140, and/or any other component of the radiotherapy system 100. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining a target position of a motion terminal (e.g., the MLC).

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing device 120 and the radiotherapy device 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
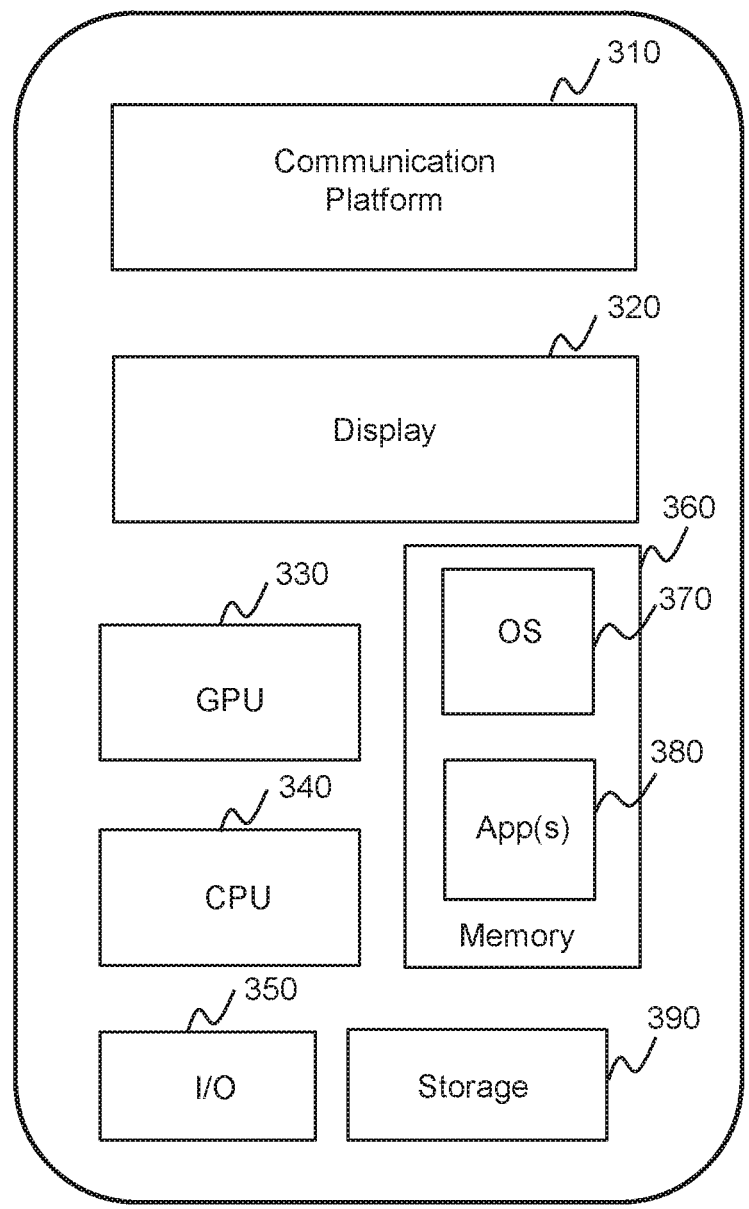
FIG. 3 is a schematic diagram illustrating exemplary hardware and/or software components of an exemplary mobile device on which the terminal(s) may be implemented according to some embodiments of the present disclosure.

FIG. 3 is a schematic diagram illustrating exemplary hardware and/or software components of an exemplary mobile device 300 on which the terminal(s) 140 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the radiotherapy system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
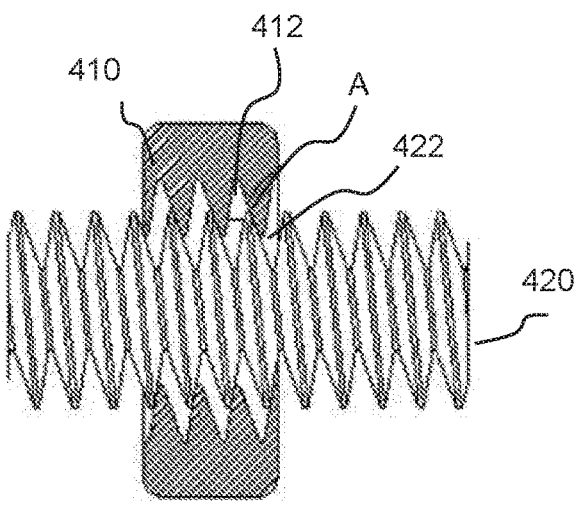
FIG. 4A-4C are schematic diagrams illustrating exemplary backlash error according to some embodiments of the present disclosure.
Figure 4B:
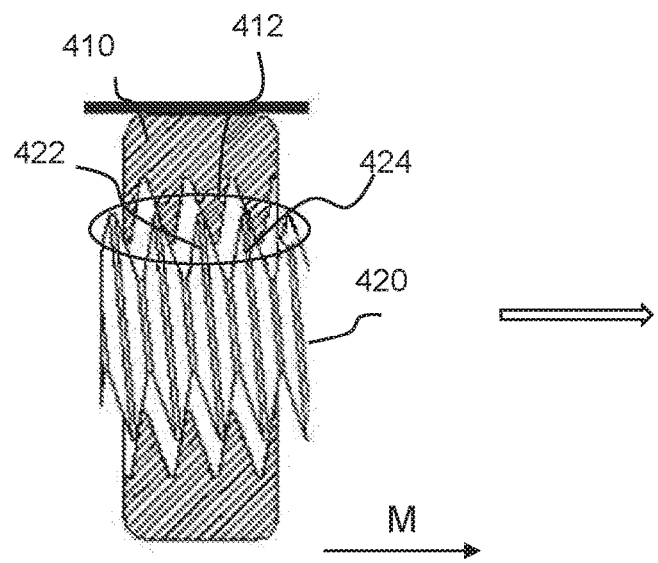
Figure 4C:
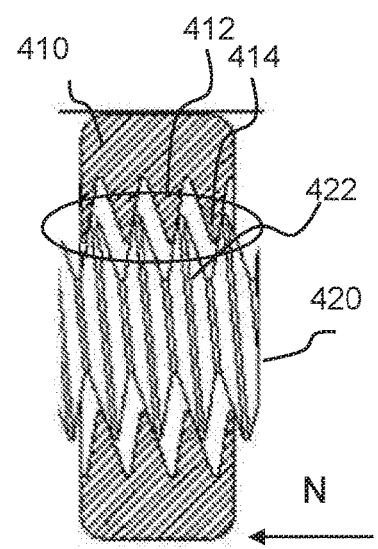

FIGS. 4A-4C illustrate exemplary backlash errors of a screw drive according to some embodiments of the present disclosure. As shown in FIG. 4A, a screw drive may include a screw nut 410 and a screw rod 420. The screw nut 410 and the screw rod 420 may each be configured with a plurality of teeth (e.g., a nut tooth 412 on the screw nut 410, a rod tooth 422 on the screw rod 420, etc.). The backlash error may occur between two teeth (e.g., the nut tooth 412 and the rod tooth 422, etc.) on the screw nut 410 and the screw rod 420 respectively when a motion terminal (e.g., a leaf) associated with the screw drive changes movement direction. As shown in FIG. 4A, two teeth (e.g., the nut tooth 412, the rod tooth 422, etc.) on the screw nut 410 and the screw rod 420 respectively are separated from each other. There is backlash represented by a gap A between the two teeth (e.g., the nut tooth 412, the rod tooth 422, etc.) on the screw nut 410 and the screw rod 420 respectively.

As shown in FIGS. 4B and 4C, when the motion terminal (e.g., a leaf) is moving along a movement direction represented by arrow M or arrow N, two teeth (e.g., a nut tooth 412, a rod tooth 422, etc.) on the screw nut 410 and the screw rod 420 respectively are contacted by each other. There is no backlash between the two teeth (e.g., the nut tooth 412, the rod tooth 422, etc.) on the screw nut 410 and the screw rod 420 respectively. The motion terminal (e.g., a leaf) may move if a driving component (e.g., a motor) associated with the motion terminal is working (e.g., rotating) as no backlash between the two teeth (e.g., the nut tooth 412, the rod tooth 422, etc.) on the screw nut 410 and the screw rod 420 respectively.

If the motion terminal as shown in FIG. 4B moves along a movement direction represented by arrow M or the motion terminal as shown in FIG. 4C moves along a movement direction represented by arrow N, there is backlash between the two teeth (e.g., the nut tooth 412 and a rod tooth 424 in FIG. 4B, a nut tooth 414 and the rod tooth 422 in FIG. 4C, etc.) on the screw nut 410 and the screw rod 420 respectively.

Figure 5:
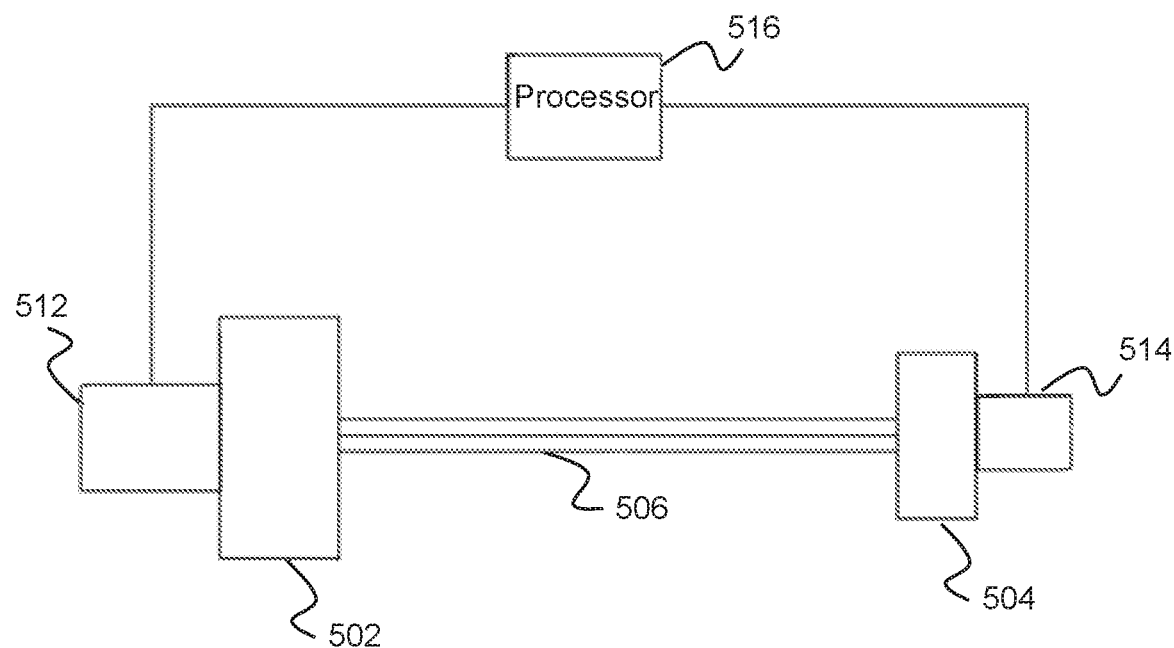
FIG. 5 is a schematic diagram illustrating an exemplary system for correcting a position error of a motion terminal according to some embodiments of the present disclosure.

FIG. 5 is a schematic diagram illustrating an exemplary system 500 for correcting a position error of a motion terminal according to some embodiments of the present disclosure. As illustrated in FIG. 5, the system 500 may include a driving component 502, a motion terminal 504, a transmission device 506, a first sensor 512, a second sensor 514, and a processor 516. The driving component 502 may be connected to the motion terminal 504 via the transmission device 506. The driving component 502 may drive the motion terminal 504 to move via actuating the transmission device 506. Merely by way of example, the driving component 502 may include a motor. The motion terminal 504 may refer to a load, such as a leaf of an MLC (e.g., a leaf of the MLC 114). In some embodiments, the transmission device 506 may include a screw drive, a gear drive, a belt drive, or the like, or any combination thereof.

In some embodiments, when the driving component 502 drives the motion terminal 504 by the transmission device 506, due to the manufacturing errors relating to the transmission device 506, an actual position of the motion terminal 504 may be inconsistent with the target position specified by the processor 516. In some embodiments, the position error of the motion terminal 504 may be caused by a backlash error relating to the driving component 502, motion terminal deformation, motion terminal positioning, horizontality, perpendicularity, or the like, or any combination thereof. The descriptions of the position error (e.g., backlash error) may be found elsewhere in this application (e.g., the descriptions of FIGS. 4A-4C).

The first sensor 512 may be associated with the driving component 502. For example, the first sensor 512 may be coupled with the driving component 502. The first sensor 512 may be configured to obtain a first displacement of the motion terminal 504 outputted by the driving component 502. As used herein, the first displacement may refer to an instruction displacement which may be used by the driving component 502 to control a movement of the motion terminal 504. For example, the motion terminal 504 may be driven by the driving component 502 to move from an initial position to a target position based on the first displacement. In some embodiments, the arrived actual position of the motion terminal 504 may deviate from the target position due to the backlash error. In some embodiments, the first sensor 512 (e.g., an encoder) may be configured to receive a calibration displacement value determined by the processor 516. The driving component 502 may further drive the motion terminal 504 to move to the target position based on the calibration displacement value. In some embodiments, the first sensor 512 may include a displacement sensor. Exemplary displacement sensors may include an encoder, a Hall sensor, an inductive sensor, a capacitive sensor, a photoelectric sensor, etc.

The second sensor 514 may be associated with the motion terminal 504. For example, the second sensor 514 may be coupled with the motion terminal 504. The second sensor 514 may be configured to obtain a second displacement of the motion terminal 504. As used herein, the second displacement may refer to an actual displacement of the motion terminal 504 from an initial position to an arrived actual position. In some embodiments, the second sensor 514 may include the displacement sensor. Exemplary displacement sensors may include but not limited that an encoder, a Hall sensor, an inductive sensor, a capacitive sensor, a photoelectric sensor, etc.

The processor 516 may be connected to and/or communicate with the first sensor 512 and/or the second sensor 514. For example, the processor 516 may obtain the first displacement and/or the second displacement from the corresponding sensor (e.g., the first sensor 512 and/or the second sensor 514). The processor 516 may determine an offset value of a position error of the motion terminal 504 and/or determine a calibration displacement (also referred herein to a calibration displacement value) based on the offset value of the position error. In some embodiments, the processor 516 may determine an offset value of a position error of the motion terminal 504 based on the first displacement and the second displacement. Further, the processor 516 may determine an offset value based on a difference between the first displacement and the second displacement. In some embodiments, the processor 516 may further determine a calibration displacement relating to the first displacement based on the offset value. For example, the processor 516 may adjust the first sensor 512 based on the offset value to determine the calibration displacement as described elsewhere in the present disclosure (e.g., FIGS. 9-11 and the descriptions thereof). As another example, the processor 516 may correct the first displacement based on the offset value to determine the calibration displacement. In some embodiment, the processor 516 may determine a target position of the motion terminal 504 based on the calibration displacement value. Furthermore, the driving component 502 may drive the motion terminal 504 to the target position.

Figure 6:
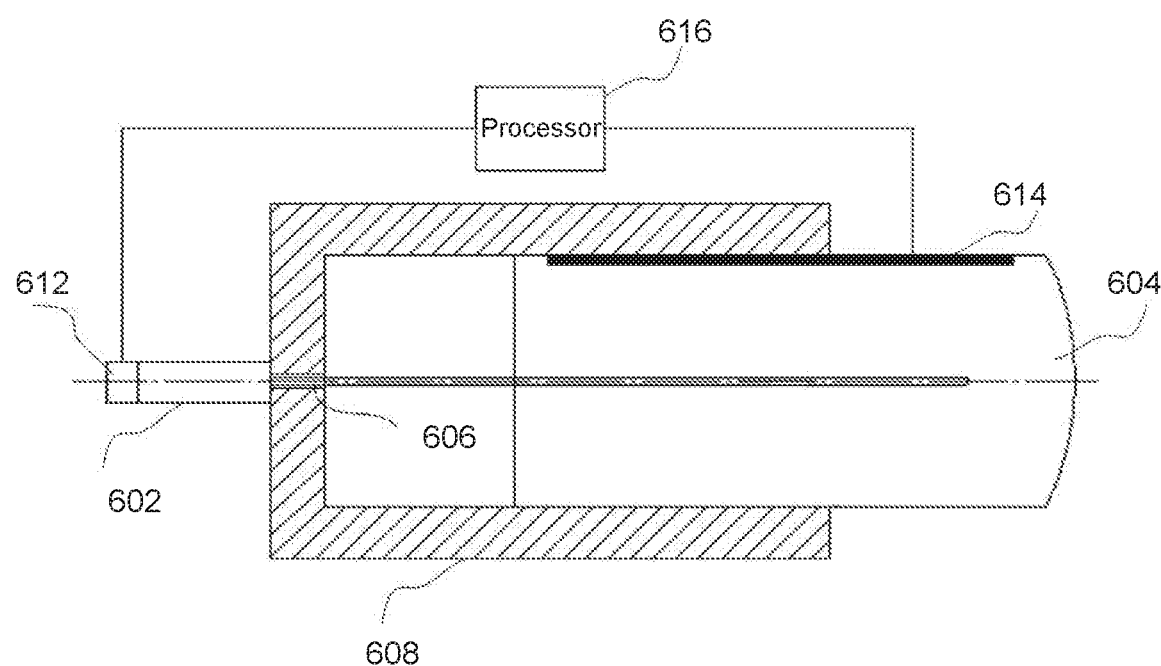
FIG. 6 is a schematic diagram illustrating an exemplary system for correcting a position error of a motion terminal in a multi-leaf collimator (MLC) according to some embodiments of the present disclosure.

FIG. 6 is a schematic diagram illustrating an exemplary system 600 for correcting a position error of a leaf according to some embodiments of the present disclosure. In some embodiments, the system 600 for correcting the position error of the motion terminal 514 may be applied to a component of the radiotherapy device, such as the multi-leaf collimator (MLC) 114 of the radiotherapy device 110 as described in FIG. 1. The MLC 114 may include the plurality of leaves to scale a radiation field. The exemplary MLC 114 may include 120 leaves. A processor (e.g., the processing device 120 or the processor 516) may control one or more driving components (e.g., motors) to drive each of the plurality of leaves by one or more transmission devices (e.g., the transmission device 506) to move. The radiation field may be expanded or narrowed when the driven leaves move to the target positions. However, backlash errors of the MLC 114 may cause the position errors associated with the plurality of leaves, which result in the actual positions of the plurality of leaves deviating from the target positions. The system 600 as illustrated in FIG. 6 may be used to correct position errors of the MLC 114. The system 600 may include a motor 602, a leaf 604, a screw drive 606, a carriage 608, an encoder 612, a Hall sensor 614, and a processor 616.

In some embodiments, the motor 602 may be connected to the leaf 604 by the screw drive 606. The leaf 604 may be configured inside of the carriage 608. The motor 602 may drive the one or more leaves 604 to move in the carriage 608 by the screw drive 606. The encoder 612 may be mounted on the motor 602. The Hall sensor 614 may be mounted on the one or more leave(s) 604. The processor 616 may be connected to and/or communicate with the encoder 612 and/or the Hall sensor 614 via wire or wireless such as a network (e.g., the network 150 shown in FIG. 1). For example, the processor 616 may exchange data and/or information (e.g., a displacement of the leaf 604) with the encoder 612 and/or the Hall sensor 614. In some embodiments, the processor 616 may communicate with any other components of the system 600, such as the driving component 602.

The processor 616 may be connected to and/or communicate with the encoder 612 and/or the Hall sensor 614. For example, the processor 616 may obtain a displacement of the leaf 604 (e.g., a first displacement from the encoder 612 and/or a second displacement from the Hall sensor 614). In some embodiments, the processor 616 may determine an offset value to correct a position error of the leaf 604 caused by the backlash error. It is understood that the backlash error may be generated during the screw drive 606 moves. In some embodiments, the processor 616 may determine the offset value of a position error of the leaf 604 based on the first displacement and the second displacement. Further, the processor 616 may determine an offset value based on a difference between the first displacement and the second displacement. In some embodiments, the processor 616 may further determine a calibration displacement value relating to the first displacement based on the offset value. For example, the processor 616 may adjust the encoder 612 based on the offset value to determine the calibration displacement. As another example, the processor 616 may correct the first displacement based on the offset value to determine the calibration displacement value. In some embodiment, the processor 616 may determine a target position of the leaf 604 based on the calibration displacement value. Furthermore, the motor 602 may drive the leaf 604 to the target position based on the calibration displacement value. More detail descriptions for correcting a position error of the leaf 604 may be found elsewhere in this disclosure (e.g., FIGS. 9-10 and the descriptions thereof).

Figure 7:
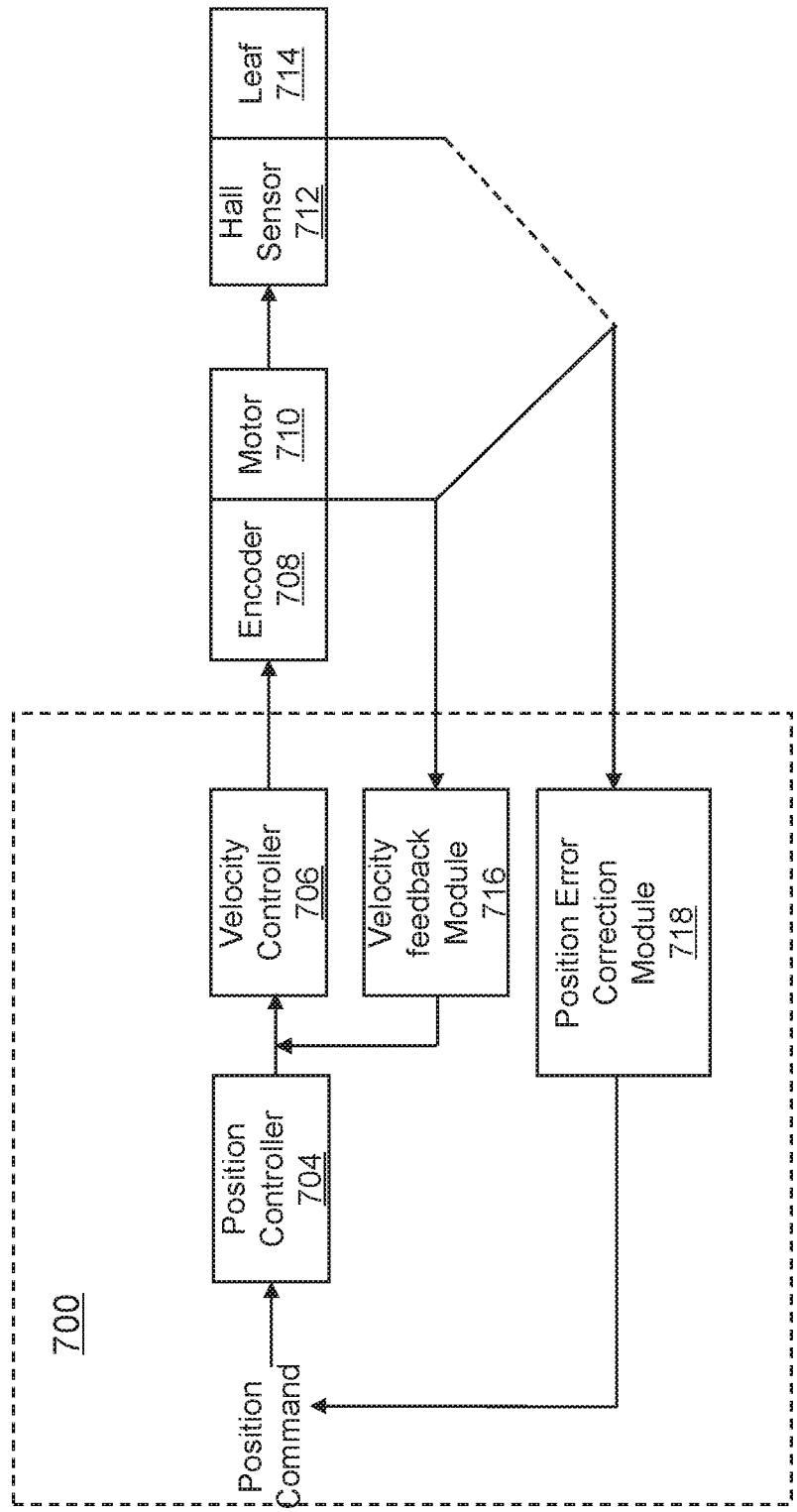
FIG. 7 is a schematic diagram illustrating an exemplary control system of the multi-leaf collimator (MLC) according to some embodiments of the present disclosure.

FIG. 7 is a schematic diagram illustrating an exemplary control system 700 of a multi-leaf collimator (MLC) according to some embodiments of the present disclosure. The processor 600 as described in FIG. 6 may perform at least one portion of functions (e.g., correcting a position error of the leaf 604) according to descriptions of the control system 700 as described in FIG. 7. As illustrated in FIG. 7, the control system 700 may include a position controller 704, a velocity controller 706, a velocity feedback module 716, and a position error correction module 718.

Figure 9:
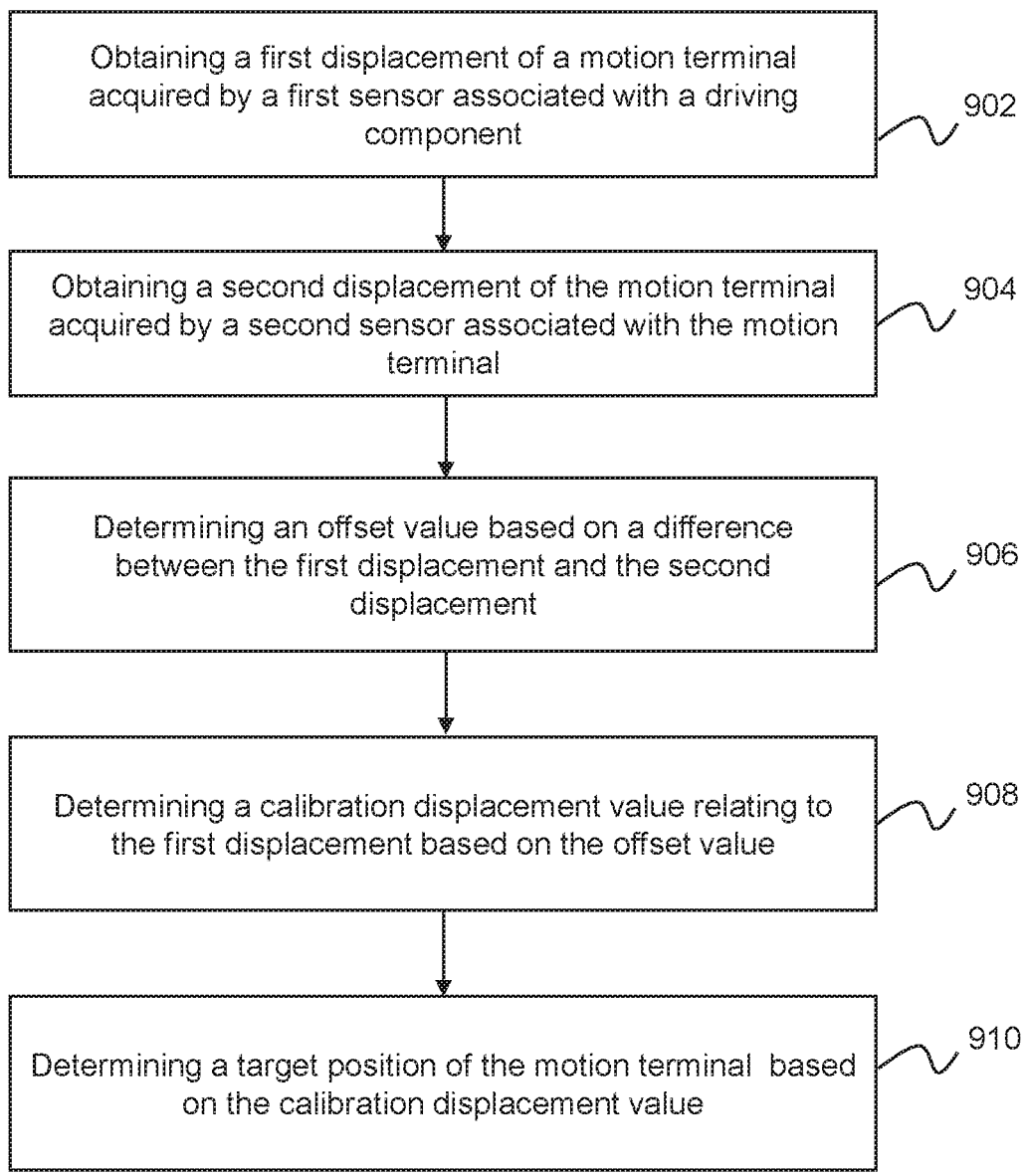
FIG. 9 is a flowchart illustrating an exemplary process for correcting a position error of a motion terminal according to some embodiments of the present disclosure.
Figure 10:
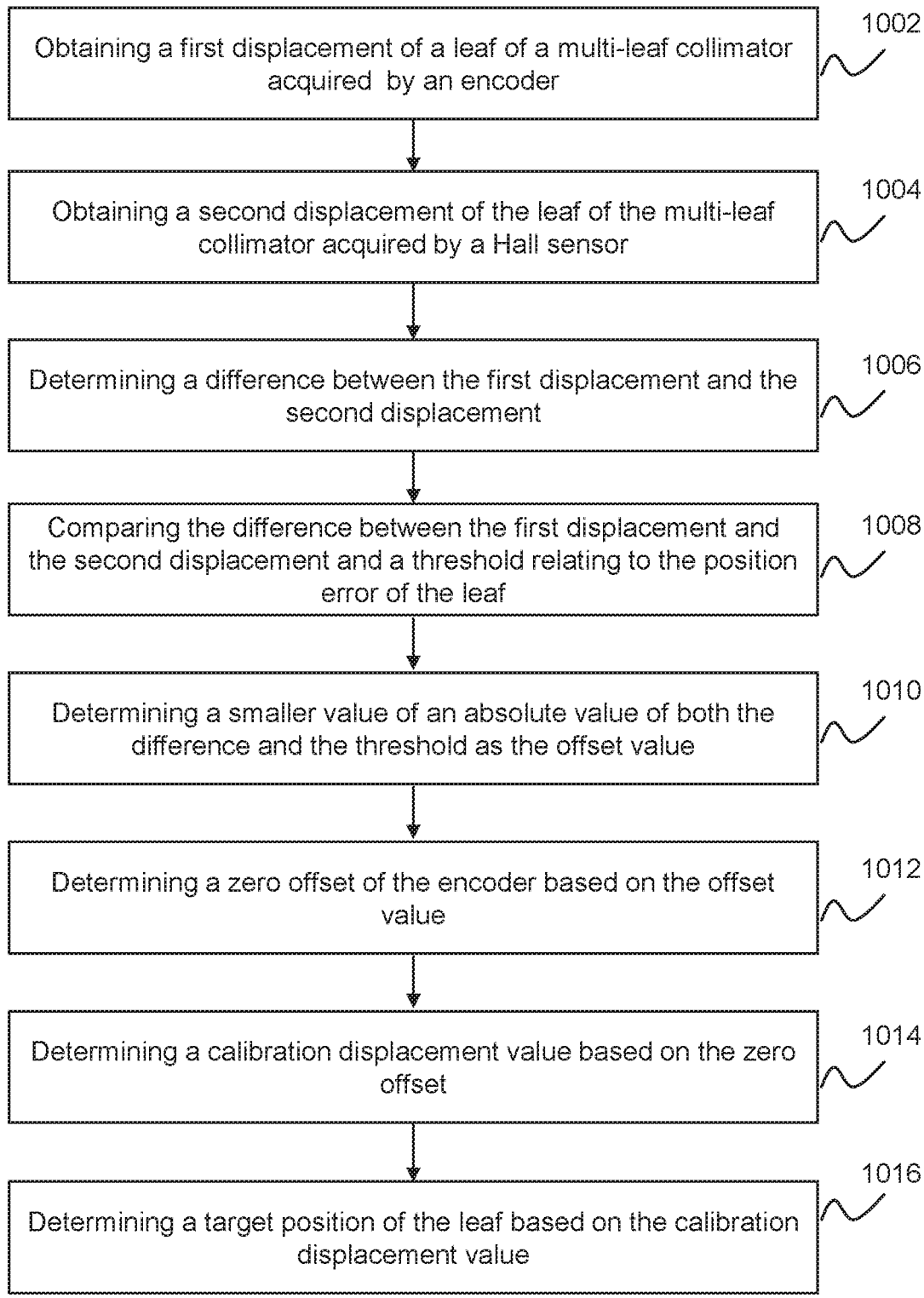
FIG. 10 is a flowchart illustrating an exemplary process for correcting a position error of a leaf of a multi-leaf collimator (MLC) according to some embodiments of the present disclosure.

The position controller 704 may receive a position command associated with a pre-determined position of a leaf 714 and control the velocity controller 706 based on the position command. In some embodiments, the position command associated with the pre-determined position of the leaf 714 may include an instruction displacement of the leaf 714 relative to the pre-determined position. In some embodiments, the position command associated with the predetermined position of the leaf 714 may be modified based on an offset value associated with the leaf 714. The offset value associated with the leaf may be determined by and/or obtained from a processor (e.g., the position correction module 718 shown in FIG. 7, or a calibration displacement value determination module 806 shown in FIG. 8) according to process 900 as illustrated in FIG. 9 and/or process 1000 as illustrated in FIG. 10. The velocity controller 706 may determine a reference rotation velocity of the motor 710 based on the position command (e.g., the instruction displacement). The velocity controller 706 may control a motor 710 to rotate according to the reference rotation velocity within a certain time to drive the leaf 714 associated with the motor 710 to move to the pre-determined position. The encoder 708 associated with the motor 710 may acquire a rotation count of the motor 710 to determine a current or real-time position or a displacement (e.g., the first displacement as described in FIG. 5 and/or FIG. 6) of the leaf 714. The Hall sensor 712 may be coupled with the leaf 714. The Hall sensor 712 may acquire a signal relating to a current or real-time position or a displacement (e.g., the second displacement as described in FIG. 5 and/or FIG. 6) of the leaf 714.

The velocity feedback module 716 may be connected to the encoder 708 and/or the Hall sensor 712. The velocity feedback module 716 may be configured to determine a current rotation velocity of the motor 710 based on the rotation of the motor 710 acquired by the encoder 708. Alternatively or simultaneously, the velocity feedback module 716 may be configured to determine a current movement velocity of the leaf 714 based on the signal acquired by the Hall sensor 712. The velocity controller 706 may acquire the current rotation velocity of the motor 710 and/or the current movement velocity of the leaf 714. Then, the velocity controller 706 may modify the reference rotation velocity of the motor 710 based on the current rotation velocity of the motor 710 and/or the current movement velocity of the leaf 714.

The position error correction module 718 may be connected to the encoder 708 and/or the Hall sensor 712. In some embodiments, the position error correction module 718 may be configured to determine an offset value of a position error of the leaf 714 using the encoder 708 and the Hall sensor 712. In some embodiments, the position error correction module 718 may determine a calibration displacement value (i.e., a calibration displacement) relating to the instruction displacement of the motor 710 based on the offset value of the position error of the leaf 714 and the instruction displacement of the motor 710 acquired by the encoder 708. The position command (e.g., the instruction displacement) may be modified based on the calibration displacement value associated with the instruction displacement of the motor 710. Then, the position controller 704 may determine a target position of the leaf 714 based on the modified position command.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the velocity feedback module 716 and the position error correction module 718 may be integrated into one single module. However, those variations and modifications do not depart the scope of the present disclosure.

Figure 8:
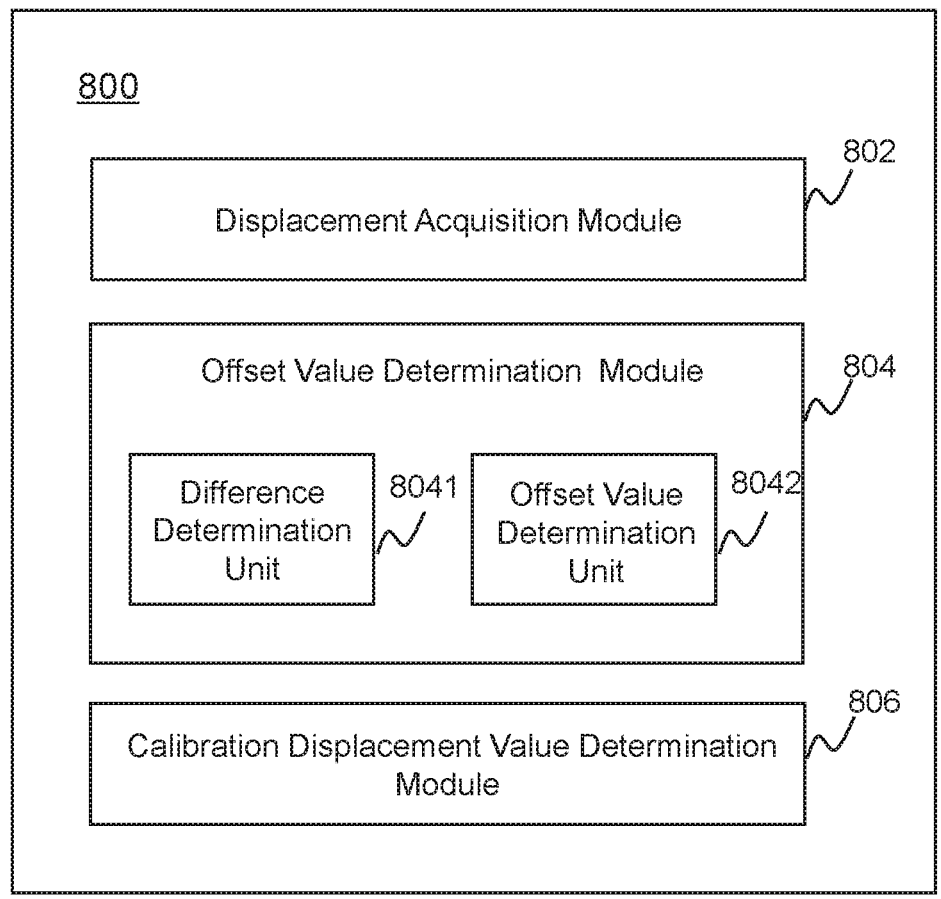
FIG. 8 is a block diagram illustrating an exemplary processing device according to some embodiments of the present disclosure.

FIG. 8 is a block diagram illustrating an exemplary processing device 120 according to some embodiments of the present disclosure. The processing device 120 may include a displacement acquisition module 802, an offset value determination module 804, and a calibration displacement value determination module 806. In some embodiments, the offset value determination module 804 may further include a difference determination unit 8041 and an offset value determination unit 8042. At least a portion of the processing device 120 may be implemented on a computing device 200 as illustrated in FIG. 2, a mobile device 300 as illustrated in FIG. 3, a processor 416 as illustrated in FIG. 4, or a processor 616 as illustrated in FIG. 6.

The displacement acquisition module 802 may obtain data relating to one or more displacements. For example, the displacement acquisition module 802 may obtain a first displacement of a motion terminal (e.g., the motion terminal 504 or the leaf 604) acquired by a first sensor (e.g., the first sensor 512 or the encoder 612). In some embodiments, the first sensor may be mounted on a driving component (e.g., a motor) associated with the motion terminal. As another example, the displacement acquisition module 802 may obtain a second displacement of the motion terminal (e.g., the motion terminal 504 or the leaf 604) acquired by a second sensor (e.g., the second sensor 514 or the Hall sensor 614). In some embodiments, the second sensor may be mounted on the motion terminal (e.g., the leaf 604). The displacement acquisition module 802 may obtain the first displacement and/or the second displacement real time or at a certain period. In some embodiments, the obtained displacements (e.g., the first displacement or the second displacement) may be transmitted to any components of the processing device 120 for further processing.

The offset value determination module 804 may determine an offset value based on the first displacement and the second displacement. More particularly, the offset value determination module 804 may determine an offset value based on a difference between the first displacement and the second displacement. In some embodiments, the offset value determination unit 8042 may compare the determined difference between the first displacement and the second displacement with an upper threshold relating to a position error of the motion terminal. The offset value determination unit 8042 may determine a smaller value of an absolute value of both the difference and the upper threshold as the offset value. In some embodiments, the offset value determination unit 8042 may transmit the determined offset value to the calibration displacement value determination module 806 for further processing.

The calibration displacement value determination module 806 may determine a calibration displacement value relating to the first displacement based on the offset value. For example, the calibration displacement value determination module 806 may determine a zero offset value associating with the first sensor (e.g., the encoder) based on the offset value. The calibration displacement value determination module 806 may determine the calibration displacement value based on the zero offset value. In some embodiments, the calibration displacement value may be equal to the zero offset value. In some embodiments, the calibration displacement value may be determined based on a product of the zero offset value and a scaling factor (e.g., 0.2, 0.3, or 0.4). As another example, the calibration displacement value determination module 806 may correct the first displacement acquired by the first sensor (e.g., the encoder) based on the offset value, and the corrected first displacement may be designated as the calibration displacement value. In some embodiments, the calibration displacement value determination module 806 may determine a target position of the motion terminal based on the calibration displacement value.

It should be noted that the description of the processing device 120 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, the offset value determination module 806 may be integrated into the calibration displacement determination module 808. As another example, the displacement acquisition module 802, the offset value determination module 804, and/or the calibration displacement value determination module 806 may be integrated into the position error correction module 718 as illustrated in FIG. 7.

FIG. 9 is a flowchart illustrating another exemplary process 900 for correcting a position error of a motion terminal according to some embodiments of the present disclosure. In some embodiments, one or more operations of process 900 illustrated in FIG. 9 may be implemented in the radiotherapy system 100 illustrated in FIG. 1. For example, the process 900 illustrated in FIG. 9 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). As another example, one or more operations of process 900 may be implemented on the same or similar processor with the processing device 120, such as the processor 516 as illustrated in FIG. 5, or the processor 616 as illustrated in FIG. 6. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 9 and described below is not intended to be limiting.

In 902, a first displacement of a motion terminal acquired by a first sensor associated with a driving component may be obtained. Operation 902 may be performed by the displacement acquisition module 802. The first sensor may be associated with and/or coupled with the driving component as described elsewhere in the present disclosure (e.g., FIGS. 5-8 and the descriptions thereof). In some embodiments, the driving component (e.g., the driving component 502) may include a motor (e.g., the motor 602). The motion terminal (e.g., the motion terminal 504) may include a leaf (e.g., the leaf 604) of an MLC (e.g., the MLC 114). The first sensor may include a displacement sensor. Exemplary displacement sensors may include but not limited that an encoder, a Hall sensor, an inductive sensor, a capacitive sensor, a photoelectric sensor, etc. In some embodiments, the first displacement may include an instruction displacement of the motion terminal output by the driving component as described elsewhere in the present disclosure (e.g., FIGS. 5-6 and the descriptions thereof). The driving component may drive the motion terminal to a target position (or a predetermined position) according to the instruction displacement. In some embodiments, a displacement of the motion terminal driven by the displacement component according to the first displacement (i.e., the instruction displacement) may be not same as the first displacement due to the position error relating to the driving component, the transmission device, and/or the motion terminal. In some embodiments, the first displacement may be predetermined by a user or according to a default setting (e.g., a treatment plan associated with an MLC) of the radiotherapy system 100.

In 904, a second displacement of the motion terminal acquired by a second sensor associated with the motion terminal may be obtained. Operation 904 may be performed by the displacement acquisition module 802. In some embodiments, the second sensor may be associated with and/or mounted on the motion terminal as described elsewhere in the present disclosure (e.g., FIGS. 5-8 and the descriptions thereof). The motion terminal may include a leaf of an MLC (e.g., the MLC 114) as illustrated in FIG. 1. The second sensor may include a displacement sensor. Exemplary displacement sensors may include an encoder, a Hall sensor, an inductive sensor, a capacitive sensor, a photoelectric sensor, etc. In some embodiments, the second sensor may include a Hall sensor. The second sensor may be same as or different from the first sensor. For example, the first sensor may include an encoder. The second sensor may include a Hall sensor. As another example, the first sensor may include a first encoder. The second sensor may include a second encoder. The second displacement may refer to an actual movement displacement of the motion terminal driven by the driving component. In some embodiments, the first displacement may be same as the second displacement. In some embodiments, the second displacement may be different from the first displacement due to a position error of the motion terminal (e.g., a backlash error of a leaf) as illustrated in FIGS. 4A-4C.

In 906, an offset value based on a difference between the first displacement and the second displacement may be determined. Operation 906 may be performed by the offset value determination module 804. More particularly, the difference determination unit 8041 in the offset value determination module 804 may determine the difference between the first displacement and the second displacement. In some embodiments, the difference between the first displacement and the second displacement may be positive or negative based on a movement direction of the motion terminal. For example, for a leaf of an MLC, if the leaf moves to narrow a radiation field, the difference between the first displacement and the second displacement may be positive. If the leaf moves to expand the radiation field, the difference between the first displacement and the second displacement may be negative.

In some embodiments, the offset value determination module 804 may designated the difference between the first displacement and the second displacement as the offset value. In some embodiments, the offset value determination module 804 may further determine the offset value based on the difference between the first displacement and the second displacement and an upper threshold relating to a position error of the motion terminal. Further, the offset value determination module 804 may compare the determined difference between the first displacement and the second displacement with an upper threshold relating to the position error of the motion terminal, and determine a smaller value of an absolute of both the difference between the first displacement and the second displacement and the upper threshold as the offset value. In some embodiments, if the determined difference between the first displacement and the second displacement is equal to the upper threshold, any one of the difference between the first displacement and the second displacement and the upper threshold may be designated as the offset value.

In some embodiments, the upper threshold may be obtained from the radiotherapy device 110, the processing device 120, the storage 130, the terminal(s) 140, the position error correction module 718, or other external storage devices. In some embodiments, the upper threshold may be set by a user or operator via the terminal 140 or according to a default setting of the radiotherapy system 100. In some embodiments, the upper threshold may be predetermined by the processing device 120, the processor 516, the processor 616, the position error correction module 718, or other external processing device. For example, the upper threshold may be predetermined by performing a plurality of measurements of a position error (e.g., a backlash error) of the motion terminal. The number of the plurality of measurements of a position error (e.g., a backlash error) of the motion terminal may exceed or equal to a threshold (e.g., 5, 10, 50, etc.). As a further example, a plurality of measured values relating to the position error (e.g., a backlash error) of the motion terminal 504 may be determined based on the plurality of measurements of a position error (e.g., a backlash error) of the motion terminal. The upper threshold may be determined based on the plurality of measured values relating to the position error (e.g., a backlash error) of the motion terminal.

In some embodiments, one of the plurality of measured values (e.g., a maximum measured value, a minimum measured value, a secondary maximum measured value, a measured value between an average value of the plurality of measured values and the maximum measured value, etc.) may be designated as the upper threshold. For example, the offset value determination module 804 may measure the backlash error for five times. Then five measured values relating to the position error may be determined. The offset value determination value module 804 may further determine an average value of the five measured values relating to the position error of the motion terminal. It should be understood that the more measured times for the backlash error, the more accurate the average value of the plurality of measured values relating to the position error. The offset value determination value module 804 may determine one of the five measured values as the upper threshold according to the average value and/or the plurality of measured values relating to the position error of the motion terminal. For example, a measured value greater than the average value and less than a maximum value of the plurality of measured values may be determined as the upper threshold. In some embodiments, the upper threshold may be calculated based on the plurality of measured values. For example, the offset value determination value module 804 may determine a product of an average value of the plurality of measured values (e.g., the five measured values) and a safety factor as the upper threshold. The safety factor may be a predetermined by the user. For example, the safety factor may be a numerical value, such as 0.2. For those skilled in the art, the safety factor may be determined by simulating a model associated with the position error based on a modeling tool. The exemplary modeling tool may include but not limited that SolidWorks, COMSOL, AutoCAD, ADAMS, ANSYS, etc. The model may include a finite element analysis (FEA) model. In some embodiments, the safety factor may be an empirical value relating to the position error.

Figure 11:
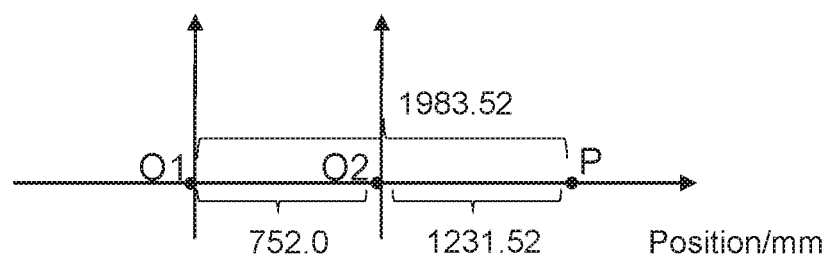
FIG. 11 is a schematic diagram illustrating an exemplary measured coordinates according to some embodiments of the present disclosure.

In 908, a calibration displacement value relating to the first displacement based on the determined offset value may be determined. Operation 908 may be performed by the calibration displacement value determination module 806. In some embodiments, the calibration displacement value determination module 806 may determine a zero offset value associating with the first sensor (e.g., the encoder) based on the offset value. In some embodiments, the zero offset value may be equal to the offset value. The calibration displacement value may be determined by adjusting the first sensor based on the zero offset value. Merely by way of example, as illustrated in FIG. 11, point O1 denotes an origin of the measured coordinates of the first sensor (e.g., the encoder), and point O2 denotes an origin of the measured coordinates of the second sensor (e.g., the Hall sensor). Point P denotes an actual position of the motion terminal. A distance from point O1 to point P denotes the first displacement (also referred to as O1P). A distance from point O2 to point P denotes the second displacement (also referred to as O2P). Assuming that the first displacement O1P is 1983.52 mm, while the second displacement O2P is 1231.52 mm. The difference between the first displacement O1P and the second displacement O2P is 752.0 mm. The difference between the first displacement O1P and the second displacement O2P, that is O1O2, may be designated as zero offset value. The calibration displacement value determination module 806 may move the origin O1 of measured coordinates of the first sensor to a reference point (i.e., point O2) that is 752.0 mm away from the origin O1. In other words, the reference point may be designated as the corrected origin of measured coordinates. In some embodiments, the position of the reference point may be consistent with the position of the origin of the measured coordinates of the second sensor. In the corrected measured coordinates of the first sensor, the displacement between the actual position (i.e. point P) and the reference point (i.e., point O2) may be designated as the calibration displacement value, such as the distance of O2P, 1231.52 mm. It should be noted that the measured coordinates as shown in FIG. 11 may be intended to be illustrative, and not to limit the scope of the present disclosure.

In some embodiments, the calibration displacement value may be determined based on a product of the zero offset value and a scaling factor (e.g., 0.2, 0.3, or 0.4). As another example, the calibration displacement value determination module 806 may determine the calibration displacement value by correcting the first displacement based on the offset value. The corrected first displacement may be designated as the calibration displacement value. For example, the calibration displacement value may equal to a difference between the first displacement and the offset value. In the case, the calibration displacement value may be equal to the actual displacement of the motion terminal.

In 910, a target position of the motion terminal based on the calibration displacement value may be determined. Operation 910 may be performed by the calibration displacement value determination module 806. In some embodiments, the target position of the motion terminal may be determined using the first sensor control the motion terminal based on the calibration displacement value. For example, the motion terminal may be driven by the driving component to move to the target position based on the calibration displacement value received by the first sensor. The target position may be determined according to an initial position of the motion terminal and the calibration displacement value. The driving component may drive the motion terminal to the target position according to an instruction displacement (i.e., the calibration displacement value) output by the processor.

FIG. 10 is a flowchart illustrating an exemplary process for correcting a position error of a leaf of a multi-leaf collimator (MLC) according to some embodiments of the present disclosure. In some embodiments, one or more operations of process 1000 illustrated in FIG. 10 may be implemented in the radiotherapy system 100 illustrated in FIG. 1. For example, the process 1000 illustrated in FIG. 10 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). As another example, one or more operations of process 1000 may be implemented on the same or similar processor with the processing device 120, such as the processor 516 as illustrated in FIG. 5, or the processor 616 as illustrated in FIG. 6. As a further example, one or more operations of process 900 may be implemented by the position error correction module 718 as illustrated in FIG. 7. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 10 and described below is not intended to be limiting.

In 1002, a first displacement of a leaf of a multi-leaf collimator (MLC) acquired by an encoder, may be obtained. Operation 1002 may be performed by the displacement acquisition module 802 as illustrated in FIG. 8. In some embodiments, the first displacement may be an instruction displacement output by the motor as described elsewhere in the present disclosure (e.g., FIGS. 5-9 and the descriptions thereof). The instruction displacement may refer to a displacement of the leaf from an initial position to a target position of the leaf in a radiotherapy planning associated with the MLC. Herein the first displacement of the leaf may be represented by X1. The first displacement (X1) of the leaf may be an ideal displacement driven by the motor. The encoder associated with the motor may acquire a rotation count of the motor to determine a current or real-time position or a displacement (e.g., the first displacement) of the leaf. In some embodiments, the first displacement (X1) of the leaf may be determined by the displacement acquisition module 802 based on the rotation count of the motor acquired by the encoder associated with the motor. For example, the displacement acquisition module 802 may communicate with the encoder via the network 150, and obtain the first displacement (X1) of the leaf acquired by the encoder via the network 150. In some embodiments, the leaf of the MLC may not be exactly driven to the target position due to a position error relating to the motor, the transmission device, and/or the leaf of the MLC. That is to say, the first displacement (X1) of the leaf determined based on the rotation count of the motor acquired by the encoder may be not consistent with the actual displacement of the leaf.

In 1004, a second displacement of the leaf of the multi-leaf collimator (MLC) acquired by a Hall sensor, may be obtained. Operation 1004 may be performed by the displacement acquisition module 802. In some embodiments, the second displacement may refer to a displacement of the leaf from an initial position to an actual position of the leaf in a radiotherapy planning associated with the MLC. Herein the second displacement of the leaf may be represented by X2. The second displacement may be an actual displacement of the leaf driven by the motor. In some embodiments, the Hall sensor may be configured on the leaf. The Hall sensor may acquire a signal relating to a current or real-time position or a displacement (e.g., the second displacement) of the leaf. In some embodiments, the second displacement of the leaf may be determined by the displacement acquisition module 802 based on the signal relating to the current or real-time position of the leaf acquired by the Hall sensor. For example, the displacement acquisition module 802 may communicate with the Hall sensor via the network 150, and obtain the second displacement X2 of the leaf acquired by the Hall sensor via the network 150.

In 1006, a difference between the first displacement and the second displacement may be determined. Operation 1006 may be performed by the difference determination unit 8041 in the offset value determination module 804. In some embodiments, the first displacement may be same as the second displacement. In some embodiments, the first displacement X1 may be different from the second displacement X2 caused by a position error during the movement of the leaf. The difference determination unit 8041 may determine the difference represented by $\Delta X$ between the first displacement X1 and the second displacement X2. For example, the difference $\Delta X$ may be determined by subtracting the first displacement X1 from the second displacement X2.

In 1008, the difference $\Delta X$ and an upper threshold relating to the position error of the leaf may be compared. Operation 1008 may be performed by the offset value determination unit 8042 in the offset value determination module 804. In some embodiments, the upper threshold may be obtained from the radiotherapy device 110, the processing device 120, the storage 130, the terminals 140, the position error correction module 718, or other external storage devices. In some embodiments, the upper threshold may be set by a user or operator via the terminal 140 or according to a default setting of the radiotherapy system 100. In some embodiments, the upper threshold may be predetermined by the processing device 120, the processor 516, the processor 616, the position error correction module 718, or other external processing device. For example, the upper threshold may be predetermined by performing a plurality of measurements of a position error (e.g., a backlash error) of the motion terminal. A number of the plurality of measurements of a position error (e.g., a backlash error) of the motion terminal may exceed or equal to a threshold (e.g., 5, 10, 50, etc.). As a further example, a plurality of measured values relating to the position error (e.g., a backlash error) of the motion terminal 504 may be determined. The upper threshold may be determined based on the plurality of measured values relating to the position error (e.g., a backlash error) of the motion terminal.

In some embodiments, one of the plurality of measured values (e.g., a maximum measured value, a minimum measured value, a secondary maximum measured value, a measured value between an average value of the plurality of measured values and the maximum measured value, etc.) may be designated as the upper threshold. For example, the offset value determination value module 804 may measure the backlash error for five times, then five measured values relating to the position error may be determined. The offset value determination value module 804 may further determine an average value of the five measured values relating to the position error of the motion terminal 504. It should be understood that the more measured times for the backlash error, the more accurate the average value of the plurality of measured values relating to the position error. The offset value determination value module 804 may determine one of the five measured values as the upper threshold according to the average value and/or the plurality of measured values relating to the position error of the motion terminal. For example, a measured value being greater than the average value and less than a maximum value of the plurality of measured values may be determined as the upper threshold. In some embodiments, the upper threshold may be calculated based on the plurality of measured values. For example, the offset value determination value module 804 may determine a product of an average value of the plurality of measured values (e.g., the five measured values) and a safety factor as the upper threshold. The safety factor may be a predetermined by the user. For example, the safety factor may be a numerical value, such as 0.2. For those skilled in the art, the safety factor may be determined by simulating a model associated with the position error based on a modeling tool. The exemplary modeling tool may include but not limited that SolidWorks, COMSOL, AutoCAD, ADAMS, ANSYS, etc. The model may include a finite element analysis (FEA) model. In some embodiments, the safety factor may be an empirical value relating to the position error.

In 1010, a smaller value of an absolute value of both the difference and the upper threshold $X_{max}$ may be determined as the offset value. Operation 1010 may be performed by the offset value determination unit 8042 in the offset value determination module 804. In some embodiments, when the absolute value of both the difference $\Delta X$ and the upper threshold $X_{max}$ are not equal to each other, the smaller value of the absolute value of both the difference $\Delta X$ and the upper threshold $X_{max}$ may be determined as the offset value C by the offset value determination unit 8042. In some embodiments, when the absolute value of both the difference $\Delta X$ and the upper threshold $X_{max}$ are equal to each other, any one value within the difference $\Delta X$ and the threshold $X_{max}$ may be determined as the offset value C by the offset value determination unit 8042.

In 1012, a zero offset of the encoder based on the offset value may be determined. Operation 1012 may be performed by the calibration displacement value determination module 806. The offset value C may represent the position error of the leaf caused by the backlash error relating to the motor, the leaf, or the transmission device. The calibration displacement value determination module 806 may determine the zero offset value of the encoder based on the offset value C. Herein the zero offset value may be represented by S. In some embodiments, the zero offset value S may be equal to the offset value C. The zero offset value S may be used to correct an origin of measured coordinates associated with the encoder. For example, as illustrated in FIG. 11, assuming that the offset value C is equal to the difference between distance O1P and distance O2P, and the offset value C is 752.0 mm, the zero offset value S may be equal to the offset value C, 752.0 mm. The calibration displacement value determination module 806 may move the origin O1 of measured coordinates of the encoder to a reference point or a corrected origin point (e.g., point O2) that is 752.0 mm away from the origin O1.

In 1014, a calibration displacement value may be determined based on the zero offset value. Operation 1014 may be performed by the calibration displacement value determination module 806. The zero offset value S may be transmitted to the encoder associated with the motor via the network 150. The origin of the measured coordinates of the encoder associated with the motor may be corrected at a position based on the zero offset value S. For example, as illustrated in FIG. 11, a corrected origin of measured coordinates of the encoder may correspond to a reference point (e.g., point O2) that is S away from the origin (e.g., point O1) of measured coordinates of the encoder along a specified direction. The specified direction may be determined based on the difference between the first displacement and the second displacement. For example, the difference between the first displacement and the second displacement may be positive or negative. The difference between the first displacement and the second displacement may be positive if the leaf moving along a movement direction is configured to narrow a radiation field. The difference between the first displacement and the second displacement may be negative if the leaf moving along a movement direction is configured to expand a radiation field. The encoder associated with the motor may be adjusted based on the corrected origin. In the corrected measured coordinates of the encoder, the displacement between the actual position (i.e. point P) and the reference point (e.g., point O2) may be designated as the calibration displacement value, such as the distance of O2P, 1231.52 mm, as shown in FIG. 11.

In 1016, a target position of the leaf based on the calibration displacement value may be determined. Operation 1016 may be performed by the calibration displacement value determination module 806. In some embodiments, the target position of the leaf may be determined using the encoder control the motion terminal based on the calibration displacement value. For example, the leaf may be driven by the motor to move to the target position based on the calibration displacement value received by the encoder. The target position may be determined according to an initial position of the motion terminal and the calibration displacement value. The driving component 502 may drive the motion terminal 504 to the target position according to an instruction displacement (i.e., the calibration displacement value) output by the processor.

It should be noted that the description of the processing device 120 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, operations 1008-1010 may be omitted. The difference between the first displacement and the second displacement may be designated as the offset value. As another example, operations 1002 and 1004 may be integrated into one single operation. Operations 1008 and 1010 may be integrated into one single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Not with standing that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A method implemented on a computing device having at least one processor and at least one computer-readable storage medium for correcting a position error for a motion terminal driven by a driving component, comprising:
   obtaining a first displacement of the motion terminal acquired by a first sensor associated with the driving component;
   obtaining a second displacement of the motion terminal acquired by a second sensor associated with the motion terminal;
   determining an offset value based on a comparison between an upper threshold relating to the position error of the motion terminal, and a difference between the first displacement and the second displacement; and
   determining a calibration displacement value relating to the first displacement based on the offset value.

2. The method of claim 1, wherein the determining the offset value based on the comparison between the upper threshold relating to the position error of the motion terminal, and the difference between the first displacement and the second displacement includes:
   determining the difference between the first displacement and the second displacement;
   comparing the difference between the first displacement and the second displacement with the upper threshold relating to the position error of the motion terminal; and
   determining a smaller value of an absolute value of both the difference and the upper threshold as the offset value.

3. The method of claim 1, wherein the upper threshold is provided by;
   determining a plurality of measured values relating to the position error of the motion terminal;
   determining an average value of the plurality of measured values relating to the position error of the motion terminal; and
   determining the upper threshold based on the plurality of measured values relating to the position error of the motion terminal, the upper threshold being greater than the average value and less than a maximum value of the plurality of measured values relating to the position error of the motion terminal.

4. The method of claim 1, wherein the upper threshold is provided by:
  determining a plurality of measured values relating to the position error of the motion terminal;
  determining an average value of the plurality of measured values relating to the position error of the motion terminal; and
  determining a product of the average value and a safety factor as the upper threshold.

5. The method of claim 1, further comprising:
  determining a target position of the motion terminal based on the calibration displacement value.

6. The method of claim 1, wherein the first sensor includes an encoder.

7. The method of claim 1, wherein the second sensor includes a Hall sensor.

8. A system, comprising:
  a motion terminal;
  a transmission component;
  a motor configured to drive the motion terminal to move based on the transmission component;
  a first sensor associated with the motor, the first sensor being configured to acquire a first displacement of the motion terminal inputted by the motor;
  a second sensor associated with the motion terminal, the second sensor being configured to acquire a second displacement of the motion terminal;
  a computer-readable storage medium storing executable instructions for correcting a position error of the motion terminal; and
  at least one processor in communication with the computer-readable storage medium, when executing the executable instructions, the at least one processor is directed to:
    obtain the first displacement of the motion terminal acquired by the first sensor associated with the motor;
    obtain the second displacement of the motion terminal acquired by the second sensor associated with the motion terminal;
    determine an offset value based on a comparison between an upper threshold relating to the position error of the motion terminal, and a difference between the first displacement and the second displacement; and
    determine a calibration displacement value relating to the first displacement based on the offset value.

9. The system of claim 8, wherein to determine the offset value based on the comparison between the upper threshold relating to the position error of the motion terminal, and the difference between the first displacement and the second displacement, the at least one processor is directed to:
  determine the difference between the first displacement and the second displacement;
  compare the difference between the first displacement and the second displacement with the upper threshold relating to the position error of the motion terminal; and
  determine a smaller value of an absolute value of both the difference and the upper threshold as the offset value.

10. The system of claim 8, wherein the upper threshold is provided by:
  determining a plurality of measured values relating to the position error of the motion terminal;
  determining an average value of the plurality of measured values relating to the position error of the motion terminal; and
  determining the upper threshold based on the plurality of measured values relating to the position error of the motion terminal, the upper threshold being greater than the average value and less than a maximum value of the plurality of measured values relating to the position error of the motion terminal.

11. The system of claim 8, wherein the upper threshold is provided by:
  determining a plurality of measured values relating to the position error of the motion terminal;
  determining an average value of the plurality of measured values relating to the position error of the motion terminal; and
  determining-a product of the average value and a safety factor as the upper threshold.

12. The system of claim 8, the at least one processor is further directed to:
  determine a target position of the motion terminal based on the calibration displacement value.

13. The system of claim 8, wherein the first sensor includes an encoder.

14. The system of claim 8, wherein the second sensor includes a Hall sensor.

15. A system, comprising:
  a radiation source;
  a multi-leaf collimator including a plurality of leaves configured to collimate a radiation field;
  a motor configured to drive a leaf to move;
  a first sensor associated with the motor, the first sensor being configured to acquire a first displacement of the leaf inputted by the motor;
  a second sensor associated with the leaf to move, the second sensor being configured to acquire a second displacement of the each of the plurality of leaves;
  a computer-readable storage medium storing executable instructions for correcting a position error of the leaf; and
  at least one processor in communication with the computer-readable storage medium, when executing the executable instructions, the at least one processor is directed to:
    obtain the first displacement of the leaf acquired by the first sensor associated with the motor;
    obtain the second displacement of the leaf acquired by the second sensor associated with the leaf;
    determine an offset value based on a comparison between an upper threshold relating to the position error of the motion terminal, and a difference between the first displacement and the second displacement; and
    determine a calibration displacement value relating to the first displacement based on the offset value.

16. The system of claim 15, wherein to determine the offset value based on the comparison between the upper threshold relating to the position error of the motion terminal, and the difference between the first displacement and the second displacement, the at least one processor is further directed to:
  determine the difference between the first displacement and the second displacement;
  compare the difference between the first displacement and the second displacement with the upper threshold relating to the position error of the motion terminal; and
  determine a smaller value of an absolute value of both the difference and the upper threshold as the offset value.

17. The system of claim 15, wherein the upper threshold is provided by:
- determining a plurality of measured values relating to the position error of the leaf;
- determining an average value of the plurality of measured values relating to the position error of the leaf; and
- determining the upper threshold based on the plurality of measured values relating to the position error of the leaf, the upper threshold being greater than the average value and less than a maximum value of the plurality of measured values relating to the position error of the leaf.

18. The system of claim 15, the at least one processor is further directed to:
- determine a target position of the leaf based on the calibration displacement value.

19. The system of claim 15, wherein the first sensor includes an encoder and the second sensor includes a Hall sensor.

20. A non-transitory computer readable medium, comprising:
- instructions being executed by at least one processor, causing the at least one processor to implement a method for correcting a position error for a motion terminal driven by a driving component, comprising:
  - obtaining a first displacement of the motion terminal acquired by a first sensor associated with the driving component;
  - obtaining a second displacement of the motion terminal acquired by a second sensor associated with the motion terminal;
  - determining an offset value based on a comparison between an upper threshold relating to the position error of the motion terminal, and a difference between the first displacement and the second displacement; and
  - determining a calibration displacement value relating to the first displacement based on the offset value.

* * * * *